United States Patent
Lundström

(10) Patent No.: US 8,587,514 B2
(45) Date of Patent: Nov. 19, 2013

(54) DEVICE FOR CONTROLLING AN EXTERNAL UNIT

(75) Inventor: Erik Lundström, Västerås (SE)

(73) Assignee: Penny AB, Västerås (SE)

( * ) Notice: Subject to any disclaimer, the term of this patent is extended or adjusted under 35 U.S.C. 154(b) by 968 days.

(21) Appl. No.: 11/992,642

(22) PCT Filed: Sep. 21, 2006

(86) PCT No.: PCT/SE2006/050346
§ 371 (c)(1),
(2), (4) Date: Jul. 27, 2010

(87) PCT Pub. No.: WO2007/037751
PCT Pub. Date: Apr. 5, 2007

(65) Prior Publication Data
US 2010/0295769 A1    Nov. 25, 2010

Related U.S. Application Data

(60) Provisional application No. 60/724,330, filed on Oct. 6, 2005.

(30) Foreign Application Priority Data
Sep. 27, 2005   (SE) ...................................... 0502116

(51) Int. Cl.
G09G 5/00    (2006.01)
(52) U.S. Cl.
USPC ............................... 345/156; 345/157; 345/8

(58) Field of Classification Search
USPC .............. 345/7, 8, 9, 156–184; 351/209, 210
See application file for complete search history.

(56) References Cited

U.S. PATENT DOCUMENTS

| | | | |
|---|---|---|---|
| 5,180,907 A * | 1/1993 | Udden et al. | 250/205 |
| 5,742,264 A | 4/1998 | Inagaki et al. | |
| 5,923,398 A | 7/1999 | Goldman | |
| 6,083,251 A * | 7/2000 | Shindo | 607/53 |
| 6,307,589 B1 * | 10/2001 | Maquire, Jr. | 348/333.03 |
| 6,636,763 B1 | 10/2003 | Junker et al. | |
| 6,637,883 B1 * | 10/2003 | Tengshe et al. | 351/210 |

(Continued)

FOREIGN PATENT DOCUMENTS

| | | |
|---|---|---|
| EP | 0468340 A2 | 1/1992 |
| EP | 1308826 A1 | 5/2003 |

(Continued)

OTHER PUBLICATIONS

PCT/ISA/210—International Search Report—Jan. 16, 2007.

(Continued)

Primary Examiner — Dmitriy Bolotin
(74) Attorney, Agent, or Firm — Venable LLP; Eric J. Franklin

(57) ABSTRACT

A device for controlling a click command controlled external unit including a portable head mounted frame, a click command detector mounted on the head mounted frame and adapted to sense tension changes of at least one muscle in the face of the user in order to detect when the user provide a click command, and a click command transmitter adapted to transmit information about detected click commands to the external unit.

20 Claims, 9 Drawing Sheets

(56) References Cited

U.S. PATENT DOCUMENTS

| | | | |
|---|---|---|---|
| 6,847,336 | B1 | 1/2005 | Lemelson et al. |
| 2001/0056225 | A1 | 12/2001 | DeVito |
| 2005/0209828 | A1* | 9/2005 | Blosser et al. ............... 702/190 |
| 2006/0252978 | A1* | 11/2006 | Vesely et al. .................. 600/27 |
| 2009/0115727 | A1* | 5/2009 | Wu ............................. 345/163 |

FOREIGN PATENT DOCUMENTS

| | | |
|---|---|---|
| GB | 2265003 A | 9/1993 |
| GB | 2396421 A | 6/2004 |
| WO | WO-9721382 A1 | 6/1997 |
| WO | WO-9905988 A2 | 2/1999 |
| WO | WO-2004045399 | 6/2004 |

OTHER PUBLICATIONS

PCT/IPEA/409—International Preliminary Report on Patentability—Jan. 29, 2008.
PCT/IPEA/408—Written Opinion of the International Preliminary Examining Authority—Oct. 22, 2007.
Ed Taylor, Hands Free Tracking, Tribune, Jan. 22, 2005.
Ir.H.J.M. Veendrick, Deep-Submicron COMS ICS, Chapters 4 and 5, 1998.

* cited by examiner

DEVICE FOR CONTROLLING AN EXTERNAL UNIT

CROSS-REFERENCE TO RELATED APPLICATIONS

This application claims priority to U.S. provisional patent application 60/724,330 filed 6 Oct. 2005 and Swedish patent application 0502116-7 filed 27 Sep. 2005 and is the national phase under 35 U.S.C. §371 of PCT/SE2006/050346.

FIELD OF THE INVENTION

The present invention relates to a device for controlling a click command controlled external unit. Such a device is adapted to upon command of a user generate and send a click command, corresponding to a click on a mouse or a click on a button, to an external unit. The button is, for example, a soft button on a graphical user interface.

PRIOR ART

It is known in the art to control a cursor and navigate on a display screen to control a computer cursor by eye movements and blinking. Such a system is, for example, advantageous for people who have muscular disabilities or people who need to have their hands free to do something else than to hold a mouse or a keyboard device, for example a pilot.

In an article "Hands-free tracking" by Ed Taylor, Tribune, Jan. 22, 2005, displayed on the Internet, with the following link: http://www.eastvalleytribune.com/index.php?sty+35151 a hardware and software system, which allows users to control a computer cursor by eye movements and blinking, is disclosed. This system is proposed to replace the mouse of a computer. The system comprises two infrared light modules that are mounted on the sides of the computer's display monitor, a camera that is placed on the keyboard to follow the movements of the user's eyes and software to make the system to work. The low-power infrared light shines on the user's eyes and creates reflections that are picked up by the infrared camera. The user can control the movement of the cursor by moving his or hers eyes over the screen and can perform the equivalent of a mouse, click by blinking. This system allows a disabled person to perform such functions as reading online books or sending e-mail messages.

A disadvantage with using eye blinking, to order a click command, is that it is difficult to distinguish an unintentional blinking from an intentional blinking. To be able to distinguish an eye blinking, intended as a click command, from an unintentional eye blinking, the intended eye blinking must have a longer duration than an unintended eye blinking. However, when the eye is closed for quite a long time, an unconscious drift of focus from the selected object will occur, and the user loses focus on his immediate task.

WO2004045399 discloses a method and installation for detecting and tracking eyes and gaze angles. When detecting the position and gaze direction or eyes, a photo sensor and light sources are placed around a display and a calculation and control unit is used. One of the light sources is placed around the sensor and includes inner and outer elements. When only the inner elements are illuminated, a strong bright eye effect in a captured image is obtained, this resulting in a simple detection of the pupils and thereby a safe determination of gaze direction. Such a system can for example be used for observing or determining the position on a monitor or display at which a computer user is looking.

OBJECTS AND SUMMARY OF THE INVENTION

The object of the present invention is to provide an improved device for controlling a click controlled external unit, which makes is possible for a user to generate a click command without using his hands.

Another object of the present invention is to provide a device that further facilitates the use of a computer, or other electronic equipment provided with a graphical interface, for persons who can't use their hands or have their hands occupied with other business.

According to the invention, the device comprises a portable head mounted frame, a click command detector mounted on the head mounted frame and adapted to sense tension changes of at least one muscle in the face of the user in order to detect when the user provide a click command, and a click command transmitter adapted to transmit information about detected click commands to the external unit.

The external unit is for example a computer, a pocket PC, a Palm Pilot, a mobile phone, a TV, a CD-player or a microwave oven, or any other electronic equipment that interacts with a user. The head mounted frame is for example a pair of spectacles, a helmet or a mesh. The invention makes it possible for a user to control an external unit by tension changes of a muscle in his face.

A click command is an equivalent to a mouse click or a push on a button, but instead of effectuating the click command by pushing a button on a mouse device or on the external unit, the user effectuates the click command by straining a specific muscle in the face. A click command detector, mounted on the head mounted frame, monitors the strain in the specific muscle. Accordingly, it is possible to control the external unit without the using the hands. If the external unit is provided with a graphical user interface having a cursor, the device allows the user to use a point and shoot method of input, i.e. by moving the cursor to an icon representing a data object at a particular location on the screen and providing a click command to perform a user command or a selection. It is possible to mount the click command detector close to the muscle to be monitored, and thereby to improve the click command detection. Thus, the user provides a click command by straining a selected muscle. The previously mentioned disadvantage with unconscious drift of focus from the selected object, and the user losing focus on his immediate task, is overcome the invention. Another advantage with the invention is that is possible to control the external unit from a large distance and the user does not have to look at the device when he/she provides the click command.

According to an embodiment of the invention, the click command detector is adapted to sense tension changes of at least one muscle in the temporal lobe, also denoted the temple, of the user. Thus, the user provides a click command by straining a selected muscle in the temporal lobe. The position of this muscle makes it easy to detect.

According to an embodiment of the invention, the click command detector comprises a first sensor adapted to sense changes of at least one muscle on the left side of the face, in order to detect when the user provide a left click command, and a second sensor adapted to sense changes of at least one muscle on the right side of the face, in order to detect when the user provide a right click command. A left click command is an equivalent to a click on the left button on the mouse, and a right click command is an equivalent to click on the right button on the mouse. Thus, the user can easily provide left and right click commands by straining muscles on different sides of the face.

According to an embodiment of the invention, the click command detector is adapted to detect tension changes above a threshold value. Preferably, the threshold value is adjustable. This embodiment makes it possible to adjust the amount of the tension changes needed to provide a click command, in order to avoid unintentional click command due to small tension changes, for example, when the user is chewing.

According to an embodiment of the invention, the external unit is an eye movement and click command controlled external unit, and the device comprises: an eye tracker unit mounted on the head mounted frame and adapted to monitor eye movements of a user, and an eye position transmitter adapted to transmit information about user eye movements to the external unit. If the external unit is provided with a graphical user interface having a cursor, it is possible to control the cursor by the tracked eye movements. The user wears the device on his/her head. By mounting the eye tracker on a head mounted device, it is possible to locate the monitor close to the eyes, and the eye tracker will follow the movements of the head, thereby improving the monitoring of the eye movements. Such a device is, for example, used for controlling the movement of an eye movement controlled cursor on a graphical user interface, for example, to a computer.

According to an embodiment of the invention, the eye tracker comprises a thermal device adapted to detect the temperature of separate parts of at least one eye, and based thereon detect movements of the pupil of the eye. Preferably, the thermal device comprises an infrared camera unit adapted to detect infrared radiation from at least on of the eyes of the user. This method provides an easy and accurate measurement of the movement of the pupil of the user. The method is user friendly, in that it does not affect the user in any negative way. Another advantage with this embodiment is that the eye measurement is independent of the surrounding light conditions, which means that no extra light source is needed. This embodiment makes is possible to measure movements of the pupil in weak light, and even when it is dark.

According to an embodiment of the invention, the infrared camera unit comprises a first infrared camera adapted to detect infrared radiation from one eye, and a second infrared camera adapted to detect infrared radiation from the another eye. The use of two separate infrared cameras detecting one eye each, improves the detection of the eye movements and provides stereopsis. Due to the vaulted shape of the eye, it is also advantageous to use more than one camera for measuring each eye, For example, to use two cameras for measuring each eye, in order to improve the measurement.

According to an embodiment of the invention, the infrared camera is a digital camera such as a CCD-camera or a CMOS-camera. Such cameras are commercially available. They are light and small, and thereby possible to carry on the head of the user and to locate very close to the eyes of the user. Further, such cameras have small power consumption, which makes them suitable to be battery powered.

According to an embodiment of the invention, the device comprises a control unit having memory means comprising one or more models of an eye, the model including reference values for the temperature of different parts of the eye, and the control unit is adapted to compare the reference values with temperature values received from the eye, and based thereon determine the position of the pupil of the user. Preferably, the model is a 3D-model.

According to an embodiment of the invention, the device further comprises: a receiver adapted to receive image signals from the external unit, and an image creator adapted to produce an image in front of the user, based on the received image signals, and the image signals from the external unit comprises signals corresponding to a graphical user interface to the external unit, which interface has an eye movement controlled cursor. An advantage with this embodiment is that is possible to control the external unit from a large distance. The user does not need to be close to the external unit, or even to look in the direction of the external unit, to be able to control it.

Preferably, the received images also comprise content. For example, the image signals comprise a text document and the graphical user interface comprises icons and menus for editing the document. This embodiment makes it possible to display the screen of the external unit in front of the user, independent of the location of the external unit. At the same time as the screen is displayed in front of the user, it is possible for the user to navigate on the screen by means of his/her eyes, and preferably also to control elements on the screen and provide commands by means of selected muscles in the face. Accordingly, it is possible to handle the external unit without using the hands. It is possible to replace a traditional keyboard, display screen and mouse with such a device. For example, the device can be used to make a phone call on the mobile phone, to write and edit a document, to write program code and to surf on the Internet.

According to an embodiment of the invention, the image creator comprises a projector adapted to project an image of the user interface on the retina of the user. Since the image is displayed on the retina of the user, no display screen in needed. Alternatively, the head mounted frame could be provided with a screen positioned in front of the user, and the image could be displayed on the screen.

According to an embodiment of the invention, the receiver comprises an optical fiber adapted to receive the image signals in one of its ends, and the projector comprises a micro-screen provided in the other end of the optical fiber. Today, the size of a micro-screen is in the order of mm and even μm. Preferably, the micro screen is a C-MOS micro screen. Thanks to the use of a C-MOS micro-screen, no extra light source is needed. The light emitted from the micro-screen is enough to send the image further. The use of an optical fiber eliminates the need of a converter between light and electromagnetism. Another advantage with the optical fiber is that it reduces the radiation directed to the head of the user. A further advantage with the optical fiber is that it makes it impossible to bug the image signals from an external system.

According to an embodiment of the invention, the projector further comprises a reflector or prism arranged to mirror the image about 90°, and a convex lens arranged so that it makes the image to pass through the pupil of the eye and so that a magnification of the image is projected on the retina of the eye. This is a simple solution, which only requires a few parts.

According to an embodiment of the invention, the head mounted frame is designed as spectacles frame. A spectacle frame is easy to carry for the user, particularly if the user already needs spectacles to correct a visual defect.

According to an embodiment of the invention, the spectacles frame comprises a front part and two bows, and the eye tracker is mounted at the front part of the spectacles frame, and the click command transmitter is mounted at the bows of the spectacles frame. Preferably, the image creator is mounted at the front part of the spectacles frame. Such a device is convenient for the user to carry and does not look so odd. If the click command detector comprises two sensors for detecting left and a right click commands, it is particularly suitable to mount the left command sensor in the left bow and the right click command sensor in the right bow.

According to an embodiment of the invention, the device is provided with a microphone, and the device is adapted to transmit signals from the microphone to the external unit. Preferably, the device is also provided with a headphone. Thus, the device could further be uses as a communication tool. This is, for example, advantageous when the external unit is mobile phone.

According to an embodiment of the invention, the device is provided with a camera arranged to have an external view from the user, and the device is adapted to transmit signals from the camera to the external unit. This is advantageous during real-time communication with other users of similar devices, or users of computer units, which are linked together via radio communication with devices according to the invention. Images can be recorded, transferred, or sent directly to other users in order to show them what is happening right now, or what has happen. This embodiment makes it possible to take a film without using the hands.

The term comprises/comprising when used in this specification is taken to specify the presence of stated features, or components. However, the term does not preclude the presence or addition of one or more additional features, integers, steps or components or groups thereof.

BRIEF DESCRIPTION OF THE DRAWINGS

The invention will now be explained more closely by the description of different embodiments of the invention and with reference to the appended figures.

DETAILED DESCRIPTION OF PREFERRED EMBODIMENTS OF THE INVENTION

In the following, an embodiment of the invention is described, which provides all of the functions: display of a graphical user interface, eye-tracking, and click command detection, integrated in one single head mounted device. The technique used is near eye technology in a head-up display (HUD) using an eye tracking system. However, according to the invention it is also possible to implement the functions separately, or in other combinations. For example, it is possible to have a head mounted device with only the eye-tracking function, a head mounted device with only the click detection function, a head mounted device with only the eye-tracking and display function, a head mounted device with only the eye-tracking and click detection function, and a head mounted device with only the display and click detection function.

Figure 1A:
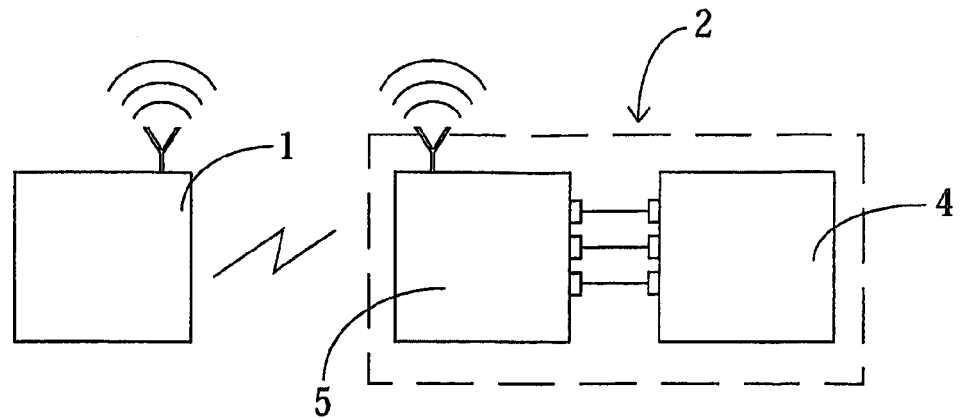
FIG. 1A shows a block diagram of an external unit and a device according to a first embodiment of the invention, which includes a head device and a modulator for converting signals between the head device and an external unit.

FIG. 1A shows an external unit 1 and a device 2, according to a first embodiment of the invention, for interacting with the external unit 2. The external unit is, for example, electronic equipment having a graphical display screen for displaying a graphical user interface for controlling the equipment and for interaction with a user, such as a computer, a mobile phone or a pocket PC. However, the external unit can also be electronic equipment, such as a microwave oven, a CD player or a TV, provided other types of user interface for controlling the equipment, for example a key set. The present invention is useful for all types of user-controlled equipment. Preferably, the external unit 1 includes a generator for generating a graphical interface including a cursor and graphical elements for controlling the external unit, a transmitter for transmitting image signals, including signals corresponding to the graphical user interface, to the device 2, a receiver for receiving signals, including information about user eye-movements and click commands, from the device 2, and a control unit for controlling the external unit 1 in response to received click commands. The graphical generator is adapted to move the cursor in response to received eye movements.

The device 2 is adapted to remotely control and interact with the external unit 1. The device 2 comprises a head mounted part 4, designed to be carried on the head of the user, and a modulator unit 5 for converting signals between the head mounted part 4 and the external unit 1. Preferably, the modulator 5 is designed to be attached to the body or to the head of the user. However, it is also possible to place the modulator 5 in the close vicinity of the user. The head mounted part 4 preferably has the shape of a pair of spectacles, but can also have the shape of a helmet or a mesh. In an embodiment of the invention, modulator unit 5 is integrated in a portable head mounted frame together with an eye tracker, a click command detector and an image creator.

In this embodiment the head mounted part 4 is provided with the following functions: display of an image in front of the user, which image shows a graphical user interface to the external unit, detection of eye movements of the user, and detection of when the user provides a click command by straining a selected muscle in the face. Preferably, the graphical user interface to the external unit has an eye movement controlled cursor. Thereby, it is possibility for the user to control elements on the displayed interface by means of his/her eyes and to provide click commands by straining a muscle in the face. Accordingly, it is possible for the user to remotely control the external unit, without having to use the hands. The modulator unit 5 transmits information about user eye movements and detected click commands to the external unit 1 and receives image signals including signals corresponding to the graphical user interface from the external unit.

In this embodiment, the external unit 1 and the modulator 5 are wirelessly connected to each other. The modulator 5 and the head mounted part 4 are physically connected to each other via a coaxial cable or an optical fiber.

Figure 1B:
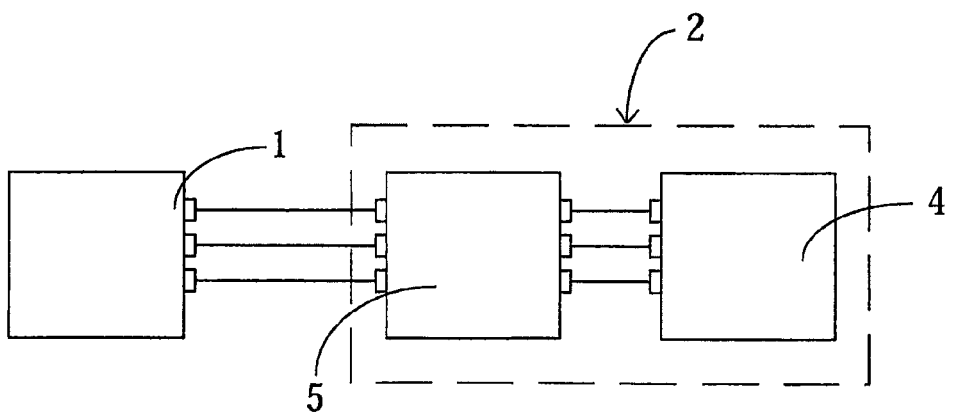
FIG. 1B shows a block diagram of an external unit and a device according to a second embodiment of the invention.

FIG. 1B shows a block diagram of an external unit and a device according to a second embodiment of the invention. In this embodiment, the external unit 1 and the modulator 5 are physically connected to each other via a coaxial cable. The modulator 5 and the head mounted part 4 are physically connected to each other via a coaxial cable an optical fiber. This embodiment it advantageous since it is difficult to bug the device.

Figure 1C:
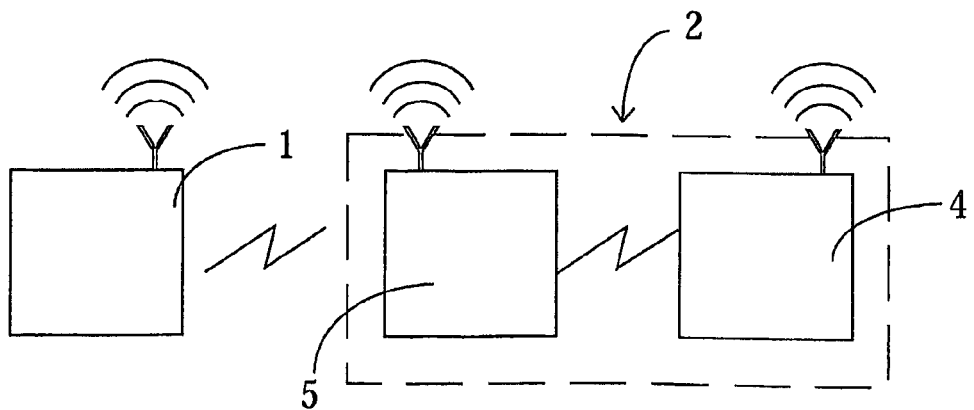
FIG. 1C shows a block diagram of an external unit and a device according to a third embodiment of the invention.

FIG. 1C shows a block diagram of an external unit and a device according to a third embodiment of the invention. In this embodiment, the external unit 1 and the modulator 5 are wirelessly connected to each other, and the modulator 5 and the head mounted part 4 are wirelessly connected to each other. The signals between the external unit 1 and modulator unit 5 are for example transferred via Bluetooth or Ultra Wide Band (UWB).

Figure 2:
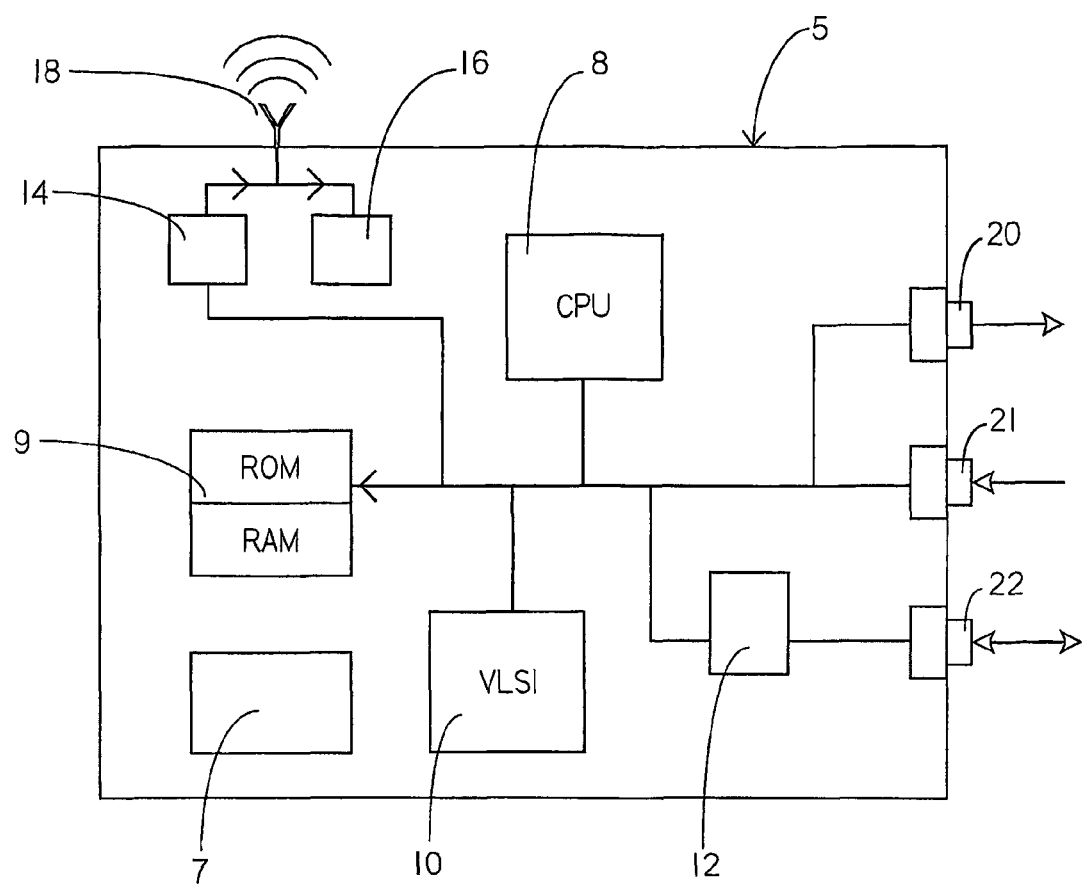
FIG. 2 shows the modulator in more details.

FIG. 2 shows the modulator 5 in more details. The modulator 5 is adapted to communicate with the external unit 1 and with the head mounted part 4. The modulator 5 comprises power supply in the form of a battery 7, a central processing unit (CPU) 8, memory means 9, including ROM and RAM memory, a Very Large Scale Integration Board (VLSI-board) 10, and a click detection unit 12. For communication with external unit, the modulator comprises a transmitter 14 for transmitting signal to the external unit, a receiver 16 for receiving signals from the external unit, and an antenna 18. For communication with the head mounted device 4, the modulator comprises an image signal transmitter 20 transmitting image signals from the external unit to the head mounted unit 4, a receiver 21 receiving signals corresponding to detected eye movements from the head mounted part 4, and a transmitter/receiver 22 for communicating click detection signals between the modulator and the head mounted part. The function of the click detection unit will be explained later. The function of the VLSI-board 10 is to handle the communication between the external unit and the head mounted part 4. The VLSI-board 10 comprises means for transforming signals from the head mounted device 4 into a suitable format for the external unit 1.

Before transmitting the image signals to the head mounted unit, the signals are transformed into a suitable format, for example into electromagnetic pulses or optical pulses. The signals, corresponding to the detected eye movements, are received as electromagnetic pulses. The click transmitter/receiver communicates electromagnetic pulses to and from the head mounted part 4. The communication between the modulator unit 5 and the head mounted part 4 is either wireless or physical, by means one or more cables.

Figure 3:
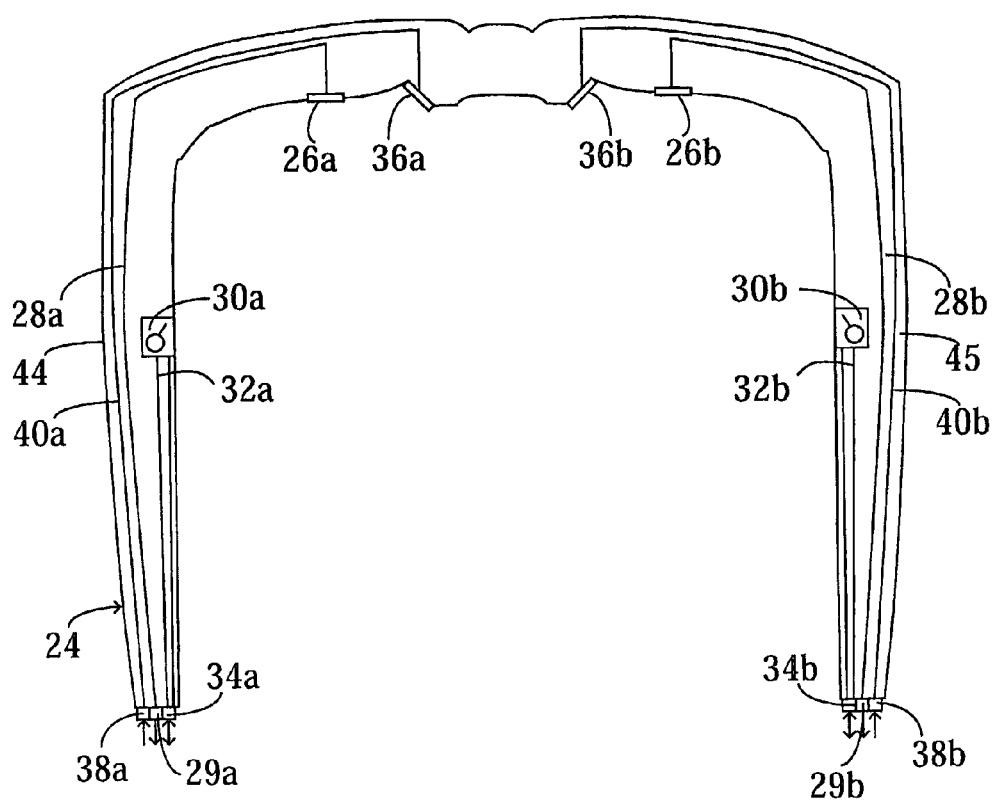
FIG. 3 shows the head device in more details.

FIG. 3 shows an example of the head mounted part 4. The head mounted part 4 comprises a portable head mounted frame 24, preferably shaped as a spectacles frame. The portable head mounted frame 24 is provided with an eye tracker unit comprising a first infrared camera 26a adapted to detect infrared radiation from one eye of the user, and a second infrared camera 26b adapted to detect infrared radiation from the other eye of the user. Thus, the infrared camera 26a is directed towards one eye of the user and the other camera 26b is directed towards the other eye of the user. Alternatively, the portable frame 24 could be provided with more than two infrared cameras, for example four infrared cameras, two of which are adapted to detect eye movements of one of the eyes, and two of which are adapted to detect the other eye. Thereby, increasing the range of user eye movements that are possible to detect. The portable frame 24 is provided with two optical fibers 28a, 28b for transferring signals from the cameras 26a-b to the modulator unit.

In order to detect eye movements, movements of the pupil is be detected. It is a well-known fact that different parts of the eye have different temperatures, independent of external conditions. By means of the infrared camera, the temperature of different parts of the eye is measured. Thereby, it is possible to distinguish the position the pupil from the rest of the eye and thereby to take a film of the movements of the pupil. The memory means 9 of the modulator 5 is provided with a database comprising one or more models of a complete eye including all parts of the eye, which may effect how the eye meets the infrared radiation in an outward direction. The model of the eye is shaped as a facetted three-dimensional image. Each facet in the image is provided with its own value, reflecting in which way energy is emitted from the part when its surface is visible, its temperature in relation to objects in the surrounding, its task in the eye, and how it acts on direct illumination. By means of a software control unit, values, calculated based on the received image from the infrared camera, are compared with reference values from the stored three-dimensional model. Movements of the pupil are calculated based on the comparison between the reference values and the calculated values from the infrared camera.

An infrared camera is a measurement instrument that makes it possible to detect infrared radiation from an object and transform it to an electrical signal, without touching the object. To reduce the size and weight of the camera it is preferable to use a digital camera based on CCD-technique or CMOS-technique. CCD-technique and CMOS-technique are, for example, described in more detail in a book written by Ir. H. J. M. Veendrick, with the title "Deep-submicron CMOS Ics", 1998 ISBN 9055761281, chapter 4 and 5. Those techniques are well suited for infrared cameras. With a digital camera technique it is possible to design cameras that is considerably smaller than cameras designed with an analog technique. The image signals from the infrared cameras 26a-b are transferred via the optical fibers 28a, 28b to transmitters 29a-b, which transform the images into electromagnetic signals and transmit them to the modulator unit 5.

The camera 26a-b is positioned in one end of the optical fiber 28a-b, and includes an image chip. The image chip consists of a plurality of light sensitive pixels, which are electrically charged so that they may generate and store electric charge from electrical particles, when the particles are illuminated. The amount of charge for each pixel is directly related to the number of photons that illuminate the pixel. The charge is read by the change of voltage in an adjacent pixel so that the charge can continue out through the sensor. The charge is converted into voltage and later digitalized with its own intensity value. This is carried out for each single pixel, to be able to create an electronic image of the eye.

The portable head mounted frame 24 is also provided with a click command detector unit adapted to sense tension changes of at least one muscle in the face of the user, in order to detect when the user provide a click command. The click command detector unit comprises a first sensor 30a adapted to sense tension changes of at least one muscle of the left side of the face, to detect when the user provides a left click command, and a second sensor 30b adapted to sense tension changes of at least one muscle of the right side of the face, to detect when the user provides a right click command. The portable frame 24 is provided with two optical fibers 32a-b, adapted to transfer signals between the click command sensors 30a-b and two contact means 34a-b. Preferably, tension changes are detected in a muscle located in an area between the eye and the ear of the user. More preferably, tension changes are detected in a muscle located in, the temporal lobe of the user. More about suitable muscles is described in connection with FIG. 10. To order a click command, the user has to strain the detected muscle. The click command sensor will be described in more detail later in connection with FIG. 9.

The portable head mounted frame 24 further comprises a projector unit adapted to project an image of the user interface of the external unit on the retina of the user, in order to make it possible for the user to control the external unit by eye movements and changes in muscle tensions. The projector unit comprises a first image projector 36a adapted to project the image on one of the eyes of the user and a second image projector 36b adapted to project the image on the other eye of the user. Image signals from the modulator unit 5 are received by the head mounted part 4 via contact members 38a-b, and the signals are transferred to the projectors via optical fibers 40a-b. The projectors will be described in more details later in connection with FIGS. 6 and 7.

Preferably, the head mounted frame 24 is designed as a spectacles frame comprising a front part 42, a left bow 44, and a right bow 45. The eye tracker unit, including the infrared cameras 26a-b is mounted at the front part 42 of the spectacles frame, the left click command detector 30a is mounted on the left bow 44, and the right click command detector 30b is mounted on the right bow 45 of the spectacles frame. To be able to detect tension changes in the selected muscle, the click command detector 30ab should be mounted so that at least a part of the detector is in contact with the muscle to be detected. Therefore it is particularly advantageous to select a muscle that is naturally in contact with the bows of a pair of spectacles. The image projectors 36a-b are mounted at the front part 42 of the spectacles frame.

The portable frame 24 is hollow in order to accommodate necessary electronic, for example the optical fibers and electronic used in connection with the click command detection, the image projection and the eye movement detection. The portable frame 24 is for example made of plastic or metal, but is preferably made of a plastic based composite material. Composite materials of today are impact resistant, cheap, and have a low weight, compared to many other materials.

Figure 4:
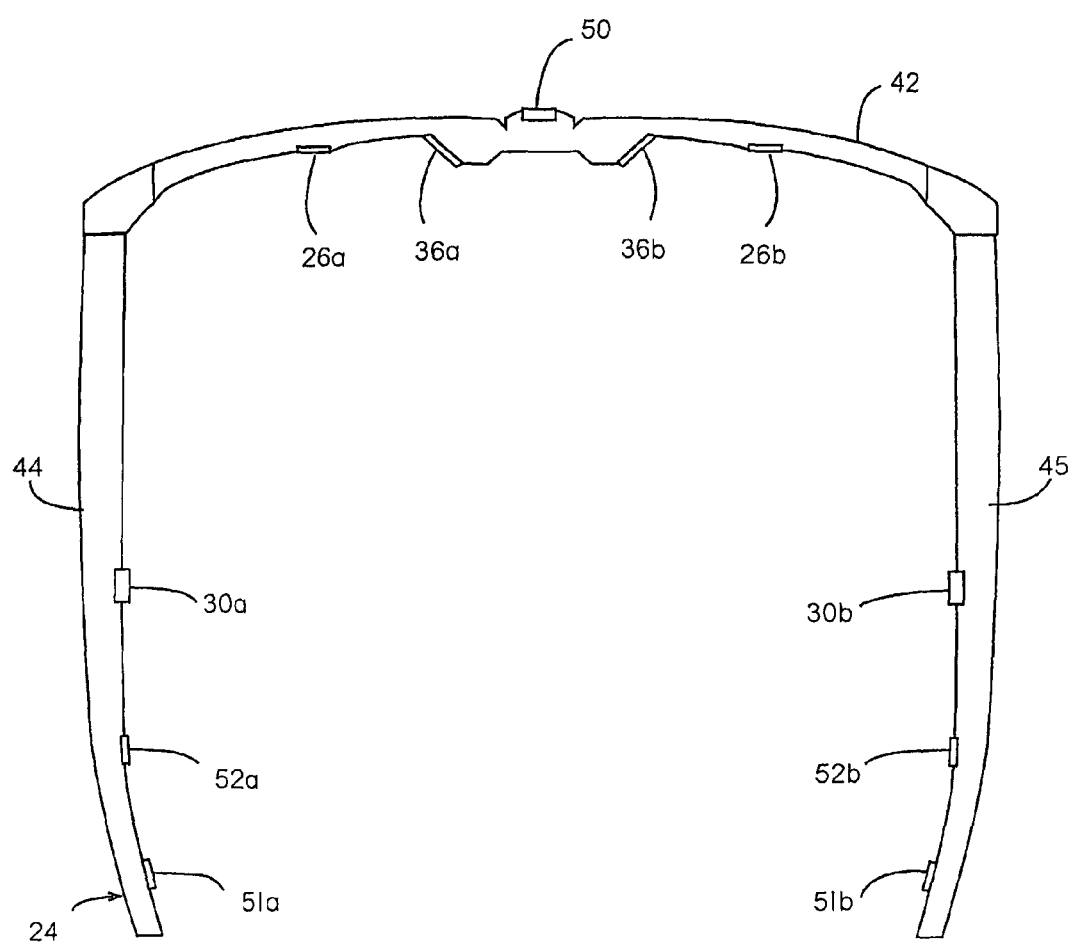
FIG. 4 shows an alternative embodiment of the head device.

FIG. 4 shows another embodiment of the head mounted part 4. The head mounted part disclosed in FIG. 4 includes the same elements as the embodiment disclosed in FIG. 3. However, the head mounted part further includes a camera 50, directed outwards, in the opposite direction of the infrared cameras 26a-b, and global position system (GPS) (not shown), by which the user may locate itself and other user on the world map. The camera 50 is positioned with its view directed away from the user so that it is possible to read the surrounding environment. Hereby it is possible for the user to take a film without using the hands. Further, the head mounted part is provided with connections to a microphone 51a-b and ear phones 52a-b, (possible for the user to select which side the microphone should be placed on) which are connected to the external unit via the modulator unit 5. The microphone connections 51a-b and earphones 52a-b provide a headset and makes it possible for the user to communicate with the external unit. This is particularly useful if the external unit is a telephone or a mobile phone. It is also possible to use the microphone 51 to provide audible commands to the external unit. In alternative embodiments, the portable head mounted frame 24 could be provided with either the camera, the GPS-function, the microphone, or the head phones, in dependence of in which application the device is to be used.

Figure 5:
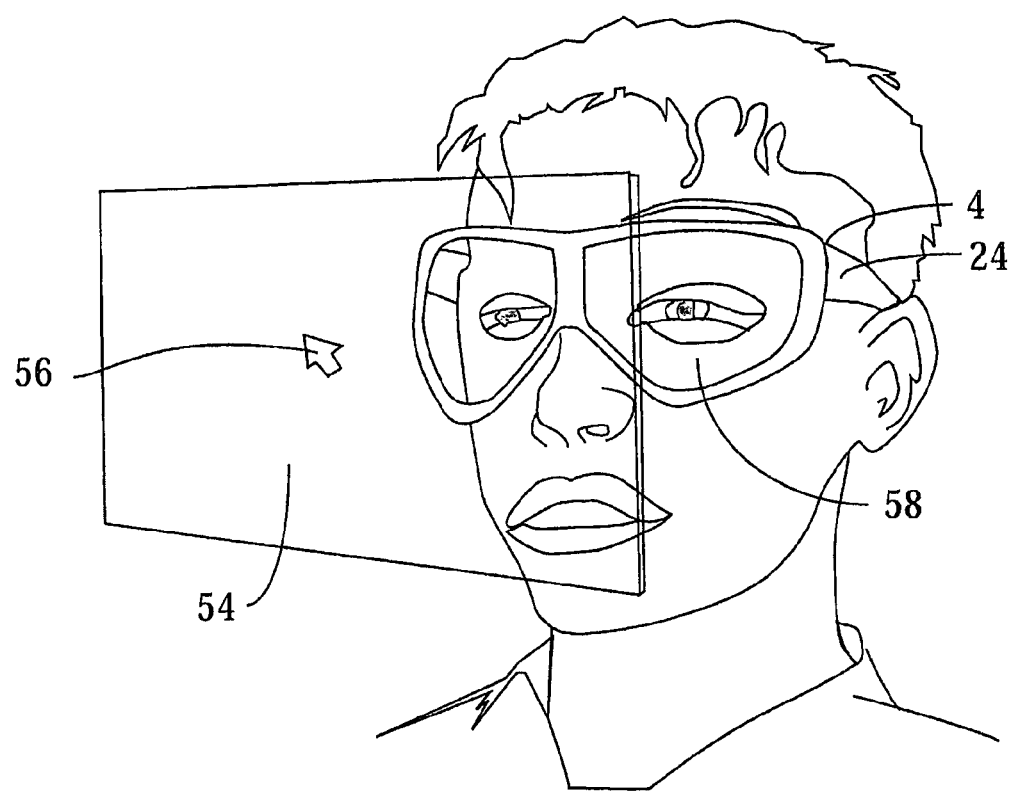
FIG. 5 shows a user wearing a device according to an embodiment of the invention.

FIG. 5 shows the user wearing the head mounted part 4. An image of the graphical screen of the external unit is projected on the retina of the user. The user experiences a large screen hanging in front of him, in the air. The screen shows content and a graphical user interface to the external unit. The graphical unit interface has a cursor 56, which is controlled by the eye movement of the user. The cursor is positioned at the spot on which the user glances at the moment. In order to move the cursor, the user moves his eyes and glance at a new spot, to which the cursor shall be moved. To provide a click command the user has to tension a selected muscle in the face, for example a muscle in the temporal lode of the user. In order to provide a left click command, the user strain a muscle on the left side of the face, and to provide a right click command, the user strain a muscle on the right side of the face. The head mounted part 4 includes the frame 24, and a pair of glasses 58. The function of the glasses 58 is to reduce light from the surroundings, so that the user can see the projected image through the glasses. The glasses 58 shall keep away light from the outside, as well as let through light from the inside.

Figure 6:
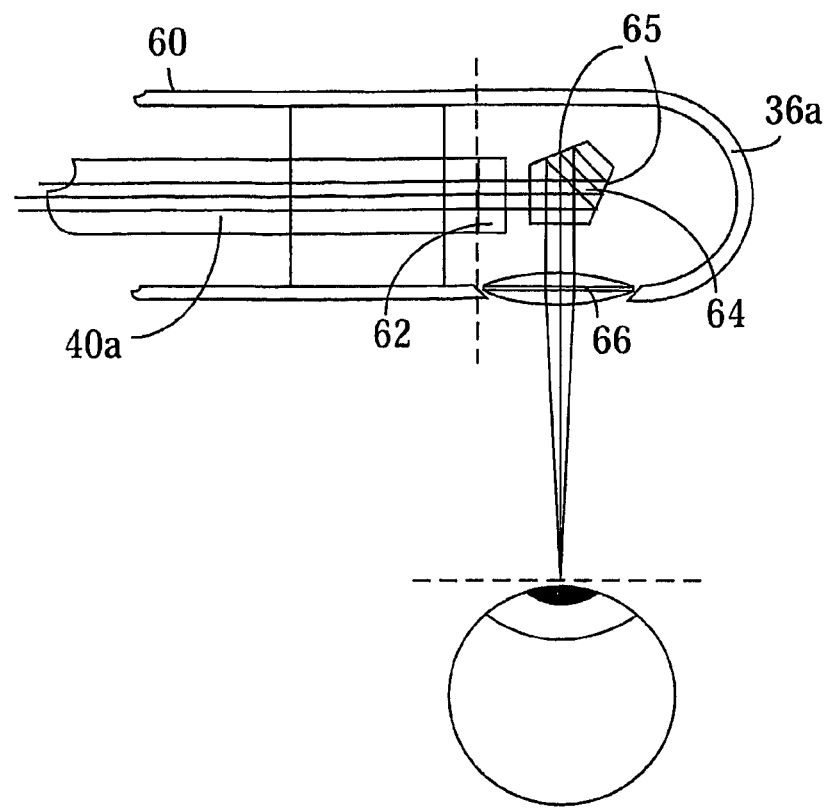
FIG. 6 shows an example of an image projector, in a view from above.

FIG. 6 shows an example of the image projector 36a-b. The aim of the projector is to project an image on the retina of the user. To make it possible to project the image on the retina, the projector must have a special design based on micro components, which are put together in a sequence inside a casing 60, having a vacuum inside. The image signals from the modulator unit 5 are converted into light signals, which are transported in the optical fiber 40a-b, which is adapted to transport visible light. The optical fiber 40a-b used for transferring signals to the projector is, for example, adapted to send an RGB image. A micro screen 62 is mounted in the other end of the optical fiber 40a-b. The light signal from the optical fiber hits the micro screen 62 and the light signal is converted into an electromagnetic pulse. The micro screen 62 is for example a CCD-screen. An advantage with a CCD-screen is that it is provided with a light source of its own. Alternatively, a coaxial cable is used instead of the optical fiber 40a-b.

The main task of the micro screen 62 is to transform the light signal from the optical fiber into a real image to be displayed to the user. If the external unit is provided with a graphical screen, it is advantageous if the image displayed to the user is the same as the image displayed on the graphical screen. With modern micro technique it is possible to produce very small (μm) screens. It is important that the screen is small; otherwise it is uncomfortable for user to wear it on the head. Possible techniques to be used for the micro screen are Complementary Metal Oxide Semiconductor (CMOS), High Temperature Poly Silicon (HTPS), Digital Light Processing (DLP) or Liquide Crystal On Silicon (LCOS).

The image projector 36 comprises a reflector 64 in the form of a penta prism. The penta prism 64 comprises two reflecting surfaces 65. The reflecting surfaces 65 are covered with a reflecting film, for example of aluminum. Advantages with the penta prism are that the image is not reflected or inverted in any direction during refraction of the image in the prism. This means that the image, which is sent through the optical fiber to the micro screen, can be sent turned the right way round. The light from the micro screen is lead into the penta prisma, and the signal is refracted 90 degrees when the light hits the reflecting surfaces 65 in the prism.

Further, the projector 36 comprises a bio-convex lens 66 arranged so that it forces the image to pass through the pupil of the eye and so that a magnification of the image is projected on the retina of the eye.

Figure 7:
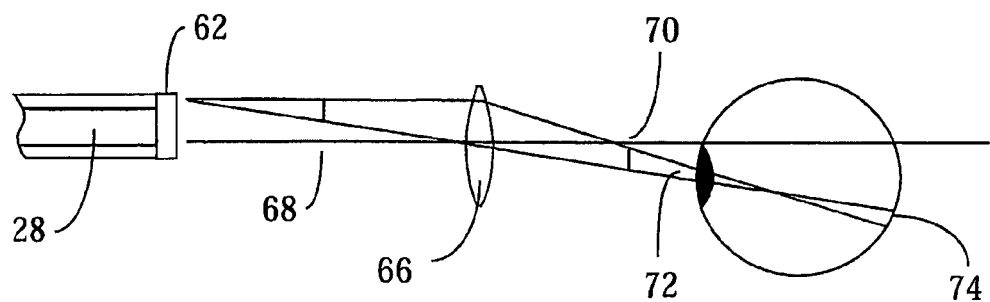
FIG. 7 shows the ray path in the image projector shown in FIG. 7, in a side view.
Figure 8:
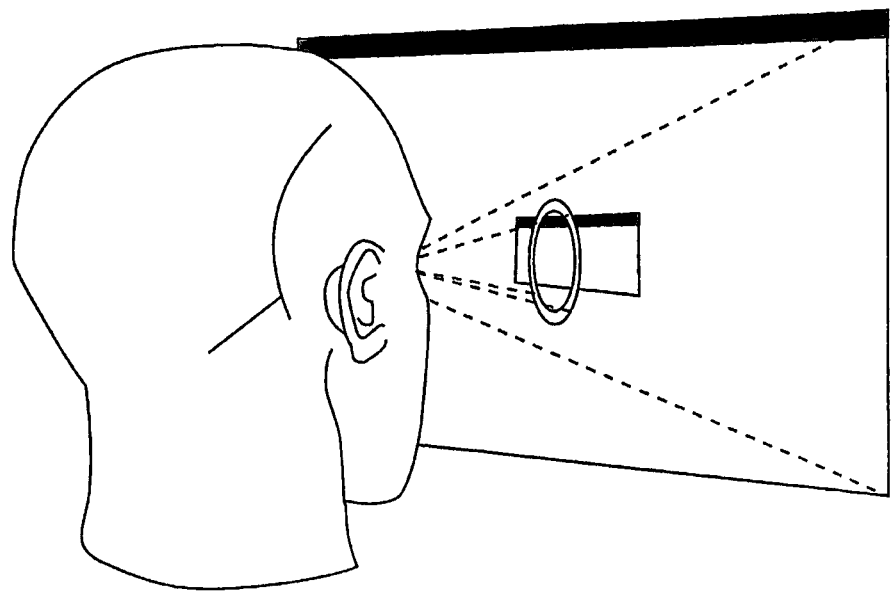
FIG. 8 shows an image of a screen projected on the retina of a user and shown in front of the user.

FIG. 7 shows the ray path through the lens 66. Using two different focus points 68,70 provides the enlargement of the image. The image signal passes through the pupil at 72 and the enlarged image is shown at 74. The image from the penta prism 64 hits the upper edge of the bio-convex lens 66. By leading the image in through the upper edge of the bio-convex lens, the light is refracted into such an angle that the image easily can be turned in the direction of the retina of the user, without any distortion of the image plane. When the image has passed through the bio-convex lens, the image is projected directly towards the retina of the user, and the image is enlarged. The user experiences an image hanging free in the air in front of the face, viewed together with the surrounding environment as shown in FIG. 8.

Figure 9:
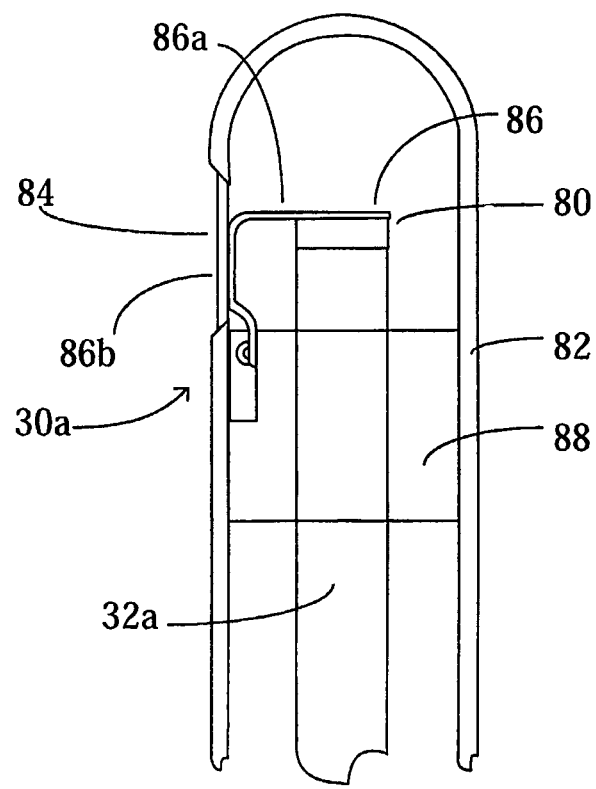
FIG. 9 shows an example of a sensor for sensing tension changes in a muscle in the face of a user.

FIG. 9 shows an example of the sensor 30*a-b* for sensing tension changes in a muscle in the temporal surface of a user, which is suitable to be mounted in the portable head mounted frame 24. The optical fiber 32*a* form a part of the sensor 30*a*, and is adapted to receive a train of light pulses in one of its ends. The other end of the optical fiber is provided with a thin film 80 of etalon. The thin etalon film 80 is transparent and thereby allows the light pulses to pass through it and out of the fiber, however with a lower frequency. The sensor 30*a* further comprises a casing 80 having vacuum inside. This casing 80 is designed to be in contact with a part of the users head, which part contains the muscle selected for sensing. The casing 80 is provided with a window 84, for example of polyurethane plastic, adapted to be in physical contact with the muscle to be sensed. Alternatively, a coaxial cable is used instead of the optical fiber 32*a*, and an electrical switch is used instead of the film 80.

The sensor 30*a* comprises a reflector 86 for reflecting the light pulses and fastening means 88 for securing the reflector 86 to the casing 82 and the optical fiber 32*a*. The reflector 86 comprises a first part 86*a*, which is arranged movable between an open position, in which the light pulse is allowed to pass out through the optical fiber 32, and a closed position, in which the light pulse is reflected, and the white light is spread in the end of the optical fiber which sends a pulse to the modulator unit that a sensing has been made. The first part 86*a* has a size corresponding to the end of the optical fiber and is adapted to function as a cover of the end of the fiber when it is in the closed position. The reflector 86 comprises a second part 86*b*, which is in contact with the window 84 and thereby is affected when the user strains a muscle in contact with the window, and accordingly effectuates the movement of the first reflector part 86 between the open and closed position.

The click detection unit 12 of the modulator unit 5 provides a train of light pulses that is transmitted to the head mounted part 4 via the transmitter 22 of the modulator and the contact mean 34*a-b* of the head mounted part. The optical fiber 32*a* is continually receiving light pulses from the modulator unit 5. When the muscle in contact with the window 84 is in a relaxed state the first reflector part 86*a* is in an open position and the light pulses are allowed to pass out of the fiber. When the user strains the muscle in contact with the window 84, the first reflector part 86*a* moves to the closed position, and thereby the intensity of the light pulse is changed. The intensity change of the light pulse will then be reflected back through the optical fiber and is transmitted back to the modulator unit 5. The click detection unit 12 comprises a light pulse detector adapted to detect the reflected light pulse. When a reflected light pulse is detected it means that the user has provided a click command. The modulator unit informs the external unit about the fact that a click command has been detected. The modulator unit also informs the external unit whether the click command is a left or a right click command, in dependence of whether the click command was provided by a muscle on the left or the right side of the face. This information is provided in the same way as for a left and right button on a traditional pointing device, such as a mouse.

For the click command sensor to function suitably and only detect signals intended for click command, it is advantageous to have software installed in the external unit, which works almost in a same manner as a normal mouse setting software do for a computer. A first time user of the system has to specify the system for their special anatomy as well as special needs. There may also be other possible settings for a user, such as which specified commands a right button click will do. For users of a special designed system a simple left and right click command may not be enough. Instead they may want to specify certain commands to the left and right sensors. All settings are saved in a flash memory for every certain user Another possibility is to let the user adjust the sensitivity of the sensor 30 in order to avoid that an unintended tension of the muscle, for example during chewing, will be detected as a click command. One possible way to design the avoidance of unconscious click commands is by time settings. The user will be able to specify his/her specialized sensitivity for the click commands by using a software timer to measure how long a muscle is tensed before a selection is made. The click command detector shall not be the one which judge when there is a click command or not, instead it should provide a continuous signal, which is later processed in order to judge if there is a click command or only a normal tension due to ordinary activities performed by the user such as chewing, talking or laughing. Another way to adjust the sensitivity of the click command detection is by directing the detection of tension changes to a specific muscle in order to shield against other muscles, which are used during normal activities. By applying the sensors in the left and right bow close to front upper end of the ear of the user it is still possible to eat food (chewing) while using the click command detector.

Figure 10:
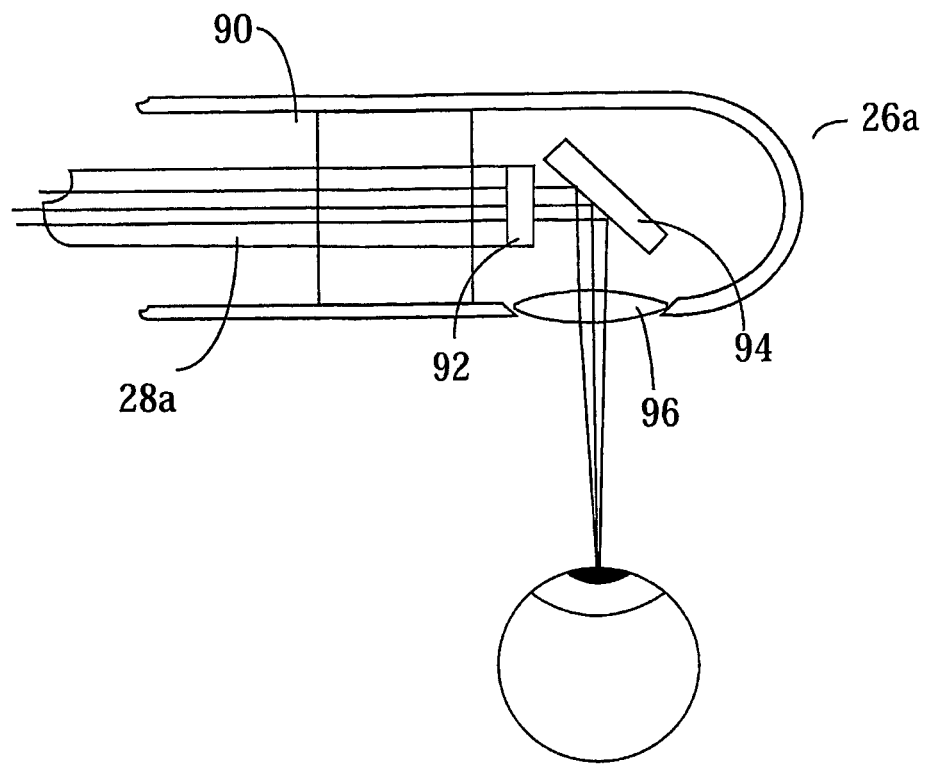
FIG. 10 shows an example of a camera for the eye tracker unit, in a view from above.

FIG. 10 shows an example of the camera device 26*a-b*. The aim of the camera is to record the position of the pupil of the user and then use the positioning for the movement of the mouse and/or navigation in a Graphical User Interface of an external unit. To make it possible to record the pupil of the eye, the camera must have a special design based on micro components, which are put together in a sequence inside a casing 90, having a vacuum inside. The camera device is recording the temperature of the different parts of the eye by using a CCD camera 92 placed at the end of an optical fiber 28*a*. Alternatively, a coaxial cable is used instead of the optical fiber 28*a*.

The main task of the CCD camera is to register the position of the pupil and send it to the modulator where it is managed. By using the wavelengths in the Middle-Infra-Red (MIR) it is possible to register the separate parts of the eye even though the user is in complete darkness or in another location where it is impossible to see the eye, i.e. heavy smoke from a fire. The camera device 26*a-b* comprises a reflector 94 and a lens 96 for directing the radiation from the eye to the camera 92.

Figure 11:
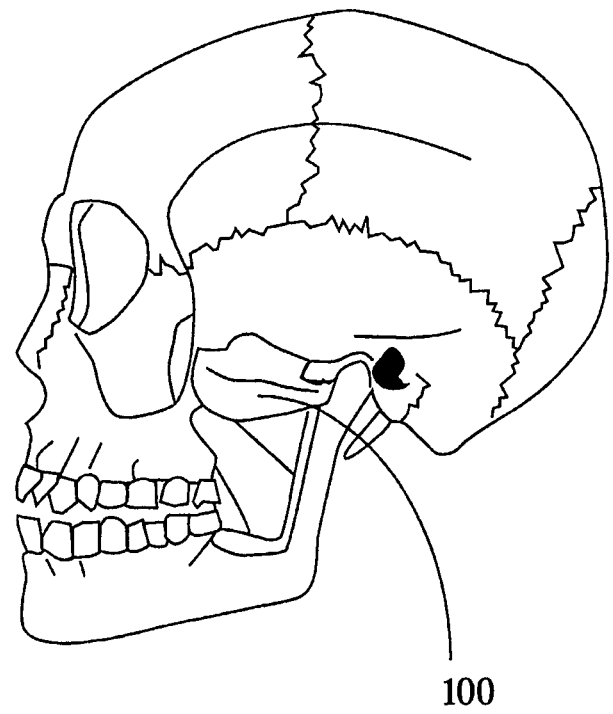
FIG. 11 shows a muscle called Lateral Ptegorya, which is suitable for providing a click-command.

FIG. 11 shows a muscle 100 called Lateral Ptegorya, which is suitable for the sensing in the mouse control unit for the left and right click command sensors 30*a-b*. Because the muscle is wide it is possible to place the sensor for the mouse control unit close to the ear to get as low tension as possible during natural chewing i.e. eating food while using the complete device. To be able to use the click command sensor and the ability to select between the left or the right button, the user has to be able to move the jaw from side to side while pushing the mandible to the upper jaw. The click command sensor is in physical contact to the Lateral Pterygoid muscle on the temporal surface of the sphenoid bone. The Lateral Pterygoid muscle acts to lower the mandible, open the jaw, and help the medial pterygoids in moving the jaw from side to side.

Mastication or chewing is the process by which food is torn and/or crushed by teeth. It is the first step of digestion. Through chewing, the food is made softer and warmer and the enzymes in saliva begin to break down carbohydrates in the food. Mastication is chiefly possible thanks to powerful muscles, masseter and temporalis, as well as smaller muscles that allow fine control. They move the mandible against the upper jaw and enable crushing of relatively hard food. In humans, the mandible is connected with the temporomandibular joint that permits forward-backward and side to side movement.

Using the muscles of mastication (chewing) for the click command detector demands a careful calculated placement. The use of the click command detector is chiefly possible by using one of the muscle groups used when chewing. Thanks to powerful muscles, masseter and temporalis, as well as smaller muscles that allow fine control. They move the mandible against the upper jaw and enable crushing of relatively hard food. Chewing food is a complex technique, muscles need to be powerful enough to break tough portions of food, yet have enough dexterity to not injure the tongue, and to clear the mouth completely. All the muscles of mastication (except stylopharyngeus) are supplied by the mandibular nerve (V3), which is a branch of the trigeminal nerve that mostly carries sensation from the face. Temporalis is a muscle attached to the temporal fossa (on the side of the skull) and connects to the coronoid process of the mandible. It acts to close the jaw, and also pull the mandible inwards (retrude it). The masseter starts at the zygomatic arch and inserts at the lateral surface of the mandible. Technique are, for example, described in more detail in a book written by Ir. H. J. M. Veendrick, with the title "Deep-submicron CMOS Ics", 1998 ISBN 9055761281, chapter 4 and 5.

The lateral pterygoid is a muscle of mastication with two heads. The upper head originates on the infratemporal surface of the sphenoid bone, and the lower head on the lateral surface of the lateral pterygoid plate; both insert onto the pterygoid fovea under the condyloid process of the mandible. It acts to lower the mandible, open the jaw, and help the medial pterygoids in moving the jaw from side to side (mastication). It is supplied by the nerve to lateral pterygoid from the mandibular nerve.

The sphenoid bone (os sphenoidale) is a bone situated at the base of the skull in front of the temporals and basilar part of the occipital. It somewhat resembles a butterfly with its wings extended, and is divided into a median portion or body, two great and two small wings extending outward from the sides of the body, and two pterygoid processes which project from it below.

The lateral pterygoid muscle on each side is one of the muscles which act upon the temporomandibular joint.
It arises from two heads:
superior head: infratemporal surface of the greater wing of the sphenoid bone
inferior head: lateral surface of lateral pterygoid plate
It passes superiorly, laterally and posteriorly to insert at two sites:
internal surface of neck of mandible
intra-articular cartilage of temporomandibular joint Lateral pterygoid is innervated by the branches from the anterior division of the mandibular nerve (CN V).
In isolation, the lateral ptergoid muscle acts to move the mandible medially. In combination, both muscles act to depress and protract the mandible. Also, they pull the joint cartilage anteriorly when the mouth opens.

Figure 12A:
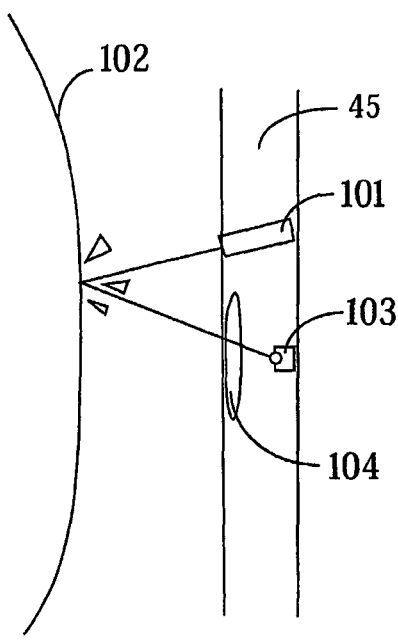
FIGS. 12a-b show another example of a sensor for sensing tension changes in a muscle in the face of a user.
Figure 12B:
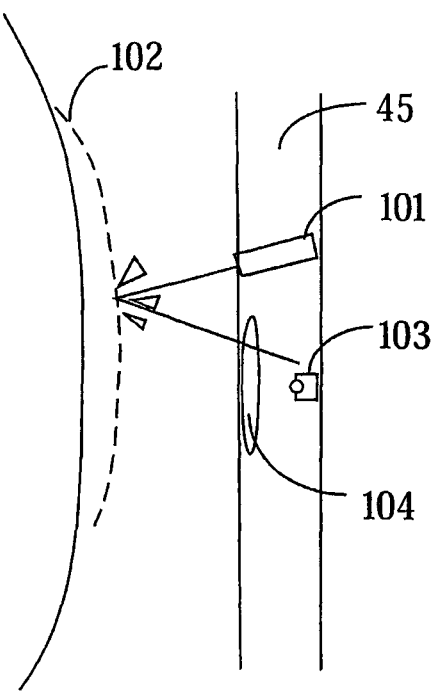

Superior head: lateral surface of the greater wing of the sphenoid
Inferior head: lateral surface of the lateral pterygoid plate
Insert together: neck of the mandibular condyle articular disk of the TMJ
Action: deviates mandible to side opposite of contraction (during chewing) opens mouth by protruding mandible (inferior head) closes the mandible (superior head)
Blood: lateral pterygoid artery
Nerve: lateral pterygoid nerve FIG. 12a-b shows an example of a light sensitive sensor for monitoring tension changes in the Lateral Ptegorya muscle in the face, which is an alternative for the click command sensor mounted on the right bow 45 of the spectacles frame. This sensor enables the same function as the click command sensor used in FIG. 9. By using a Light Emitting Diode (LED) 101 a point of light is transmitted to the user temple muscle 102. By using a one dimensional camera 103 recording the spot of light through a bioconvex lens 104, it is possible to detect when the muscle is tensed or not. FIG. 12a shows normal status, i.e. the muscle is relaxed and no selection has been made. Normal status means that the camera 103 detects light from the LED.

FIG. 12b shows how the selection is made using the LED 101 and the camera. The tension of the temple muscle 102 moves the exposure where the LED hits the temple muscle. When the camera 103 does not detect a light from the LED, a signal to the click detection unit 12 in the modulator is sent that a click command has been made.

In a basic version of the device according to the invention, all cables are of a coaxial type and no optical fibre is used for transferring any type of signal. Instead of using an infrared camera, a camera operating in the range of visible light is used. The eyes are illuminated with infrared light in order to detect the position of the pupil and thereby enabling eye tracking. The click-sensor is of a simple model including a simple on/off-switch, which turns on and off in dependence of whether the muscle in tensed or relaxed.

In an extended version, the device according to the invention, comprises an ear phone and a microphone to make it possible for the user to communicate with other users.

In an extended version, the device according to the invention, optical fibre is used for transferring any data to and from the different units in the spectacle frame. The infrared technique described above is used for detecting eye movements. The device also comprises a camera for taking photos, or taking films of the environment and a built in Global Positioning System (GPS).

The present invention is not limited to the embodiments disclosed but may be varied and modified within the scope of the following claims. For example the sensor for sensing tension changes in a muscle may include a system that is based on a Fabry-Perot cavity attached to an optical fibre. An external pressure can deflect one of the walls, the membrane in the cavity. Light that travels trough the fibre enters the cavity. When the depth of the cavity changes, the conditions for optical interference inside the cavity change. Intensity variations in the reflected light can then be detected by a photodetector at the opposing fibre end.

The invention claimed is:

1. A device for controlling a click command controlled external unit, the device comprising:
 a portable head mounted frame,
 a click command detector mounted on said head mounted frame and adapted to sense tension changes of at least one muscle in a face of a user in order to detect when the user provides a click command, and
 a click command transmitter adapted to transmit information about detected click commands to the external unit,
 wherein said click command detector is configured to transmit a point of light to said muscle in the face of the user, such that the point of light is reflected in the face of the user, the click command detector comprises a detector arranged such that it detects the reflected point of light when the muscle is relaxed, and it does not detect the reflected point of light when the muscle is tensed, and the command detector is configured to generate a signal when no light is detected.

2. The device according to claim 1, wherein said click command detector is adapted to sense tension changes of at least one muscle in the temporal lobe of the user.

3. The device according to claim 1, wherein said click command detector comprises a first sensor adapted to sense tension changes of at least one muscle on a left side of the face, in order to detect when the user provides a left click command, and a second sensor adapted to sense tension changes of at least one muscle on a right side of the face, in order to detect when the user provides a right click command.

4. The device according to claim 1, wherein said click command detector is adapted to detect tension changes above a threshold value.

5. The device according to claim 1, wherein said external unit is an eye movement and click command controlled external unit, the device further comprising:
   an eye tracker unit mounted on said head mounted frame and adapted to monitor eye movements of the user, and
   an eye position transmitter adapted to transmit information about user eye movements to said external unit.

6. The device according to claim 5, wherein said eye tracker unit is adapted to detect the temperature of separate parts of at least one eye, and based on the detected temperature detect movements of a pupil of the eye.

7. The device according to claim 6, wherein said eye tracker unit comprises an infrared camera adapted to detect infrared radiation from at least en one of the eyes of the user.

8. The device according to claim 7, wherein said eye tracker unit comprises a first infrared camera adapted to detect infrared radiation from one eye, and a second infrared camera adapted to detect infrared radiation from the another eye.

9. The device according to claim 6, wherein said infrared camera is a digital camera.

10. The device according to claim 9, wherein said a digital camera comprises a CCD-camera or a CMOS-camera.

11. The device according to claim 5, further comprising:
    a control unit comprising memory means comprising at least one model of an eye, the at least one model including reference values for the temperature of different parts of the eye, wherein the control unit is adapted to compare said reference values with temperature values received from the eye, and based thereon determine the position of the pupil of the user.

12. The device according to claim 1, further comprising:
    a receiver adapted to receive image signals from the external unit, and
    an image creator adapted to produce an image in front of the user, based on said received image signals,
    wherein said image signals from the external unit comprises signals corresponding to a graphical user interface to said external unit, which interface comprises an eye movement controlled cursor.

13. The device according to claim 12, wherein said image creator comprises a projector adapted to project an image of said user interface on a retina of the user.

14. The device according to claim 13, wherein said receiver comprises an optical fiber adapted to receive the image signals in one of its ends, and said projector comprises a microscreen provided in the other end of said optical fiber.

15. The device according to claim 12, wherein said projector further comprises a reflector or prism arranged to mirror the image about 90°, and a convex lens arranged to make the image to pass through the pupil of the eye such that a magnification of the image is projected on the retina of the eye.

16. The device according to claim 1, wherein said head mounted frame comprises a spectacles frame.

17. The device according to claim 16, wherein the spectacles frame comprises a front part and two bows, and said eye tracker unit is mounted at the front part of the spectacles frame, and said click command detector is mounted at the bows of the spectacles frame.

18. The device according to claim 17, wherein said image creator is mounted at the front part of the spectacles frame.

19. The device according to claim 1, further comprising:
    a microphone, wherein the device is adapted to transmit signals from the microphone to the external unit.

20. The device according to claim 1, further comprising:
    a camera (50) arranged to have an external view from the user, wherein the device is adapted to transmit signals from the camera to the external unit.

* * * * *

UNITED STATES PATENT AND TRADEMARK OFFICE
CERTIFICATE OF CORRECTION

| | | |
|---|---|---|
| PATENT NO. | : 8,587,514 B2 | Page 1 of 1 |
| APPLICATION NO. | : 11/992642 | |
| DATED | : November 19, 2013 | |
| INVENTOR(S) | : Lundstrom | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1637 days.

Signed and Sealed this
Fifth Day of May, 2015

Michelle K. Lee
*Director of the United States Patent and Trademark Office*